(12) United States Patent
Miura et al.

(10) Patent No.: US 7,393,937 B2
(45) Date of Patent: Jul. 1, 2008

(54) N-ACETYLGLUCOSAMINE DERIVATIVES AND USE THEREOF

(75) Inventors: Kyoko Miura, Odawara (JP); Tetsuya Sayo, Odawara (JP); Shingo Sakai, Odawara (JP); Shintaro Inoue, Odawara (JP)

(73) Assignee: Kao Corporation, Tokyo (JP)

( * ) Notice: Subject to any disclaimer, the term of this patent is extended or adjusted under 35 U.S.C. 154(b) by 391 days.

(21) Appl. No.: 10/531,176

(22) PCT Filed: Jul. 25, 2003

(86) PCT No.: PCT/JP03/09428

§ 371 (c)(1),
(2), (4) Date: Apr. 11, 2005

(87) PCT Pub. No.: WO2004/033474

PCT Pub. Date: Apr. 22, 2004

(65) Prior Publication Data

US 2006/0020127 A1     Jan. 26, 2006

(30) Foreign Application Priority Data

Oct. 9, 2002   (JP) ............. 2002-295733
Jan. 17, 2003  (JP) ............. 2003-009365
Mar. 24, 2003  (JP) ............. 2003-079595

(51) Int. Cl.
*C07H 15/00*   (2006.01)
*C07H 17/00*   (2006.01)
*C07H 17/02*   (2006.01)
*A01N 43/04*   (2006.01)
*A61K 31/70*   (2006.01)
*C07H 5/04*    (2006.01)
*C07H 5/06*    (2006.01)
*C08B 37/00*   (2006.01)

(52) U.S. Cl. ............... 536/17.2; 536/55.2; 514/25; 514/62

(58) Field of Classification Search ............... None
See application file for complete search history.

(56) References Cited

FOREIGN PATENT DOCUMENTS

| EP | 0402776 A2 | * | 12/1990 |
| EP | 1 075 836 A2 | | 2/2001 |
| JP | 62-36306 A | | 2/1987 |
| JP | 2-243611 A | | 9/1990 |
| JP | 8-143588 A | | 6/1996 |
| JP | 2001-2551 A | | 1/2001 |
| WO | WO 00/51553 A1 | * | 9/2000 |

OTHER PUBLICATIONS

Boullanger et al. Carbohydrate Research 278(1995) 91-101.*
Shimizu. JP 02243611, Sep. 1990, English Translation.*
Noriaki et al. JP 10139793, May 1998, Machine Translation.*
Hare et al. Biochemistry 1994, 33, 10137-10148.*
Lambright et al. Biochemistry 1985, 24, 910-914.*
Mishima et al. JP 62036306, Feb. 1987, English translation.*
Giovanni Nicolosi et al., "Enzymatic procedure catalysed by lipase from Candida Antarctica for the regioprotection—deprotection of glucosamine", Tetrahedron: Asymmetry 10 (1999), pp. 2891-2897.
Jon K. Fairweather et al., "The Asymmetric dihydroxylation of Some Alkenyl 2-Acetylamino-2-deoxy-β-D-glucopyranosides: the Preparation of Optically Pure Epoxides as Putative Inhibitors of Chitinases", Aust. J. Chem. (1998), vol. 51 No. 6, pp. 471-482.
Shingo Sakai et al., "Hyohi Saibo Hyaluronic-san Sansei Sokushin Sayo o Matsu Ten'nengata N-Acetylglucosamine", Fine Chemical, Dec. 15, 2001, pp. 5-11, vol. 30, No. 22.
Shingo Sakai et al., "Metabolism of Hyaluronic Acid and Wrinkle Formation", Fragrance Journal, Apr. 15, 1998, pp. 49-58, vol. 26, No. 4, Fragrance Journal Ltd.
Bio Industry, CMC Co., Ltd., May 1, 1991, pp. 66(346)-68(348), vol. 8, No. 5.
Ludger J.M. Meyer et al., "Age-Dependent Changes of Hyaluronan in Human Skin", The Journal of Investigative Dermatology, Apr. 15, 1994, pp. 385-389, vol. 102, No. 4.
Takuo Tsuji, "Physiological Aging of Skin: Difference From Photoaging", Clinical Dermatology, Igaku-Shoin Ltd., Special Edition, Apr. 15, 1997, pp. 53-57, vol. 51, No. 5.

* cited by examiner

*Primary Examiner*—Shaojia Anna Jiang
*Assistant Examiner*—Layla Bland
(74) *Attorney, Agent, or Firm*—Foley & Lardner LLP

(57) ABSTRACT

The present invention relates to An N-acetylglucosamine derivative represented by the following formula (1), and a hyaluronic acid production promoting agent containing the same and a skin external preparation containing the same:

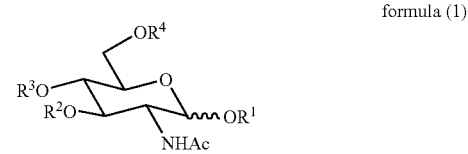

formula (1)

wherein $R^1$ is a hydrogen atom or an alkyl group having 2 to 18 carbon atoms; $R^2$, $R^3$, and $R^4$ are hydrogen atoms or acyl groups having 2 to 18 carbon atoms and may be all the same or different from others; the steric structure at position 1 may be α or β; provided that $R^1$, $R^2$, $R^3$, and $R^4$ must not be all hydrogen atoms.

It is intended to provide an easily available hyaluronic acid production promoting agent and a skin external preparation whereby the production of hyaluronic acid can be promoted in the skin and thus the skin can be maintained in a vital and moist state so that it is expected that the human skin can be prevented from age.

2 Claims, 4 Drawing Sheets

# N-ACETYLGLUCOSAMINE DERIVATIVES AND USE THEREOF

TECHNICAL FIELD

The invention relates to an N-acetylglucosamine derivative, and a hyaluronic acid production-promoting agent or a skin external preparation containing the derivative. The invention provides a skin external preparation capable of retaining the vital and moist skin.

BACKGROUND ART

Hyaluronic acid is a high molecular weight polysaccharide having a high water retention capability and has drawn attention as a very important extracellular matrix component in the skin (Shingo SAKAI, Shintaro INOUE, Metabolism of Hyaluronic Acid and Wrinkle Formation, Fragrance Journal, Fragrance Journal Ltd., vol. 26, no. 4, 49-58, Apr. 15, 1998).

Further, hyaluronic acid has been known to have many functions such as maintaining cells, retaining smoothness and suppleness of the skin, rendering the skin resistant to external force such as mechanical force and preventing the infection with pathogenic bacteria (BIO INDUSTRY, CMC Co., Ltd, vol. 8 no. 5, 66(346)-68(346), May 1, 1991).

On the other hand, it is reported that the intensity of the hyaluronic acid staining observed in the intercellular part of the epidermis decreases with aging (Ludger J. M. Meyer and Robert Stern, Age-Dependent Changes of Hyaluronan in Human Skin, The Journal of Investigative Dermatology, The society for Investigative Dermatology, Inc, Vol. 102, No. 4, pp. 385-389, April 1994), and that hyaluronic acid is hardly detected in the part affected by solar elastosis caused by ultraviolet radiation (Takuo TSUJI, Physiological Aging of Skin: Difference from Photo-aging, Clinical Dermatology, Igaku-Shoin Ltd., Special Edition, vol. 51, no. 5, 53-57, Apr. 15, 1997) and accordingly it is considered that the drying and the deterioration of the vital properties and the elasticity of the skin are caused and consequently wrinkles are increased. For the improvement of such conditions, cosmetics containing hyaluronic acid has been applied to keep the moisture retention capability of the skin surface; however, hyaluronic acid, which is a high molecular weight molecule, is hard to penetrate into the skin, and thus, the fundamental improvement cannot be expected. Accordingly, it is highly expected to develop a substance which can fundamentally improve the skin function by increasing the hyaluronic acid synthesizing capability of the cells by themselves.

Retinoic acid has been known as a hyaluronic acid production-promoting substance in the epidermis. Retinoic acid originally exists in the epidermis and is a substance involved in the proliferation and the differentiation of the epidermal cells. However, retinoic acid has the skin irritation properties. From this point of view, it is desired to find a hyaluronic acid production-promoting substance with which such problems can be avoided.

On the other hand, it has been reported that N-acetylglucosamine, which is a saccharide constituting hyaluronic acid, can promote hyaluronic acid production in the cultured epidermal cells about 1.5-times at a concentration of 5 mmol/L independently from the cell proliferation (Fine Chemical, CMC Co., Ltd., vol. 30, no. 22, 5-11, Dec. 15, 2001). However, a high concentration of N-acetylglucosamine is required to exert the hyaluronic acid production-promoting effect and accordingly, it is desired to develop a material which has an sufficient effect even at lower concentrations in order to apply in the broader fields such as the field of cosmetics and pharmaceuticals.

DISCLOSURE OF THE INVENTION

Accordingly, the object of the invention is to provide a hyaluronic acid production-promoting agent and a skin external preparation which are expected to retain the vital and moist skin and improve wrinkles by promoting hyaluronic acid production and have a higher effect than N-acetylglucosamine.

In view of the above state of the art, the present inventors have diligently studied seeking means of solving the conventional problems. Consequently, they have found that the particular compounds enumerated below can very easily and strongly promote the hyaluronic acid production in the epidermis and dermis, and thus has accomplished the present invention.

That is, the invention provides an N-acetylglucosamine derivative represented by the following formula (1), a skin external preparation containing the N-acetylglucosamine derivative, and a hyaluronic acid production-promoting agent containing the N-acetylglucosamine derivative as active ingredient:

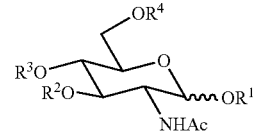

formula (1)

wherein $R^1$ is a hydrogen atom or an alkyl group having 2 to 18 carbon atoms; $R^2$, $R^3$, and $R^4$ are hydrogen atoms or acyl groups having 2 to 18 carbon atoms and may be all the same or different from others; the steric structure at position 1 may be α or β; provided that $R^1$, $R^2$, $R^3$, and $R^4$ must not be all hydrogen atoms.

The invention provides preferably an N-acetylglucosamine derivative represented by the following formula (2) or (3), a skin external preparation containing the N-acetylglucosamine derivative, and a hyaluronic acid production-promoting agent containing the N-acetylglucosamine derivative as active ingredient:

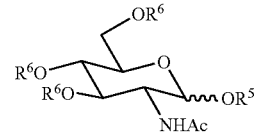

formula (2)

wherein $R^5$ is an alkyl group having 2 to 18 carbon atoms; $R^6$ is a hydrogen atom or an acetyl group; and the steric structure at position 1 may be α or β: and

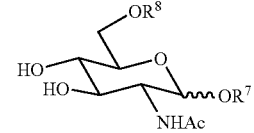

formula (3)

wherein $R^7$ is a hydrogen atom or an alkyl group having 2 to 18 carbon atoms; $R^8$ is an acyl group having 2 to 18 carbon atoms; and the steric structure at position 1 may be α or β.

Particular examples of the N-acetylglucosamine derivative represented by the above-mentioned formula (1), or (2) or (3) are those represented by the following formulas (4) to (15):

formula (4)

[structure: sugar with OH, HO, HO, NHAc, OC8H17]

wherein the steric structure at position 1 may be α or β;

formula (5)

[structure: sugar with OCC7H15 ester, HO, HO, NHAc, OH]

wherein the steric structure at position 1 may be α or β;

formula (6)

[structure: sugar with OCC7H15 ester, HO, HO, NHAc, OC8H17]

wherein the steric structure at position 1 may be α or β;

formula (7)

[structure: sugar with OH, HO, HO, NHAc, OC4H9]

wherein the steric structure at position 1 may be α or β;

formula (8)

[structure: sugar with OH, HO, HO, NHAc, OC5H11]

wherein the steric structure at position 1 may be α or β;

formula (9)

[structure: sugar with OH, HO, HO, NHAc, OC12H25]

wherein the steric structure at position 1 may be α or β;

formula (10)

[structure: sugar with OCC15H31 ester, HO, HO, NHAc, OH]

wherein the steric structure at position 1 may be α or β;

formula (11)

[structure: sugar with OH, HO, HO, NHAc, O-geranyl group]

wherein the steric structure at position 1 may be α or β;

formula (12)

[structure: sugar with OAc, AcO, AcO, NHAc, OC2H5]

wherein the steric structure at position 1 may be α or β;

formula (13)

[structure: sugar with OAc, AcO, AcO, NHAc, OC5H11]

wherein the steric structure at position 1 may be α or β;

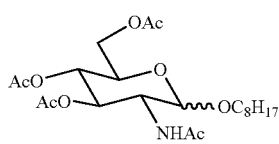

formula (14)

wherein the steric structure at position 1 may be α or β; and

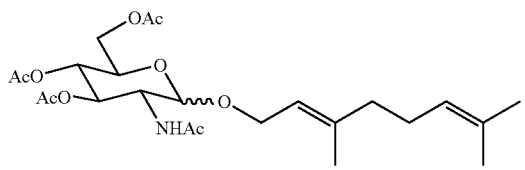

formula (15)

wherein the steric structure at position 1 may be α or β.

Further, the invention relates to a hyaluronic acid production-promoting agent and a skin external preparation containing the N-acetylglucosamine derivative represented by the following formula (16) as active ingredient:

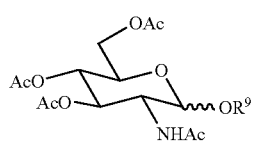

formula (16)

wherein $R^9$ is an acyl group having 2 to 16 carbon atoms and the steric structure at position 1 may be α or β.

Particular examples of the N-acetylglucosamine derivative represented by the above-mentioned formula (16) are those represented by the following formula (17);

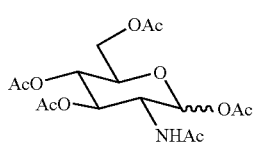

formula (17)

wherein the steric structure at position 1 may be α or β.

BEST MODE FOR CARRYING OUT THE INVENTION

Figure 1:
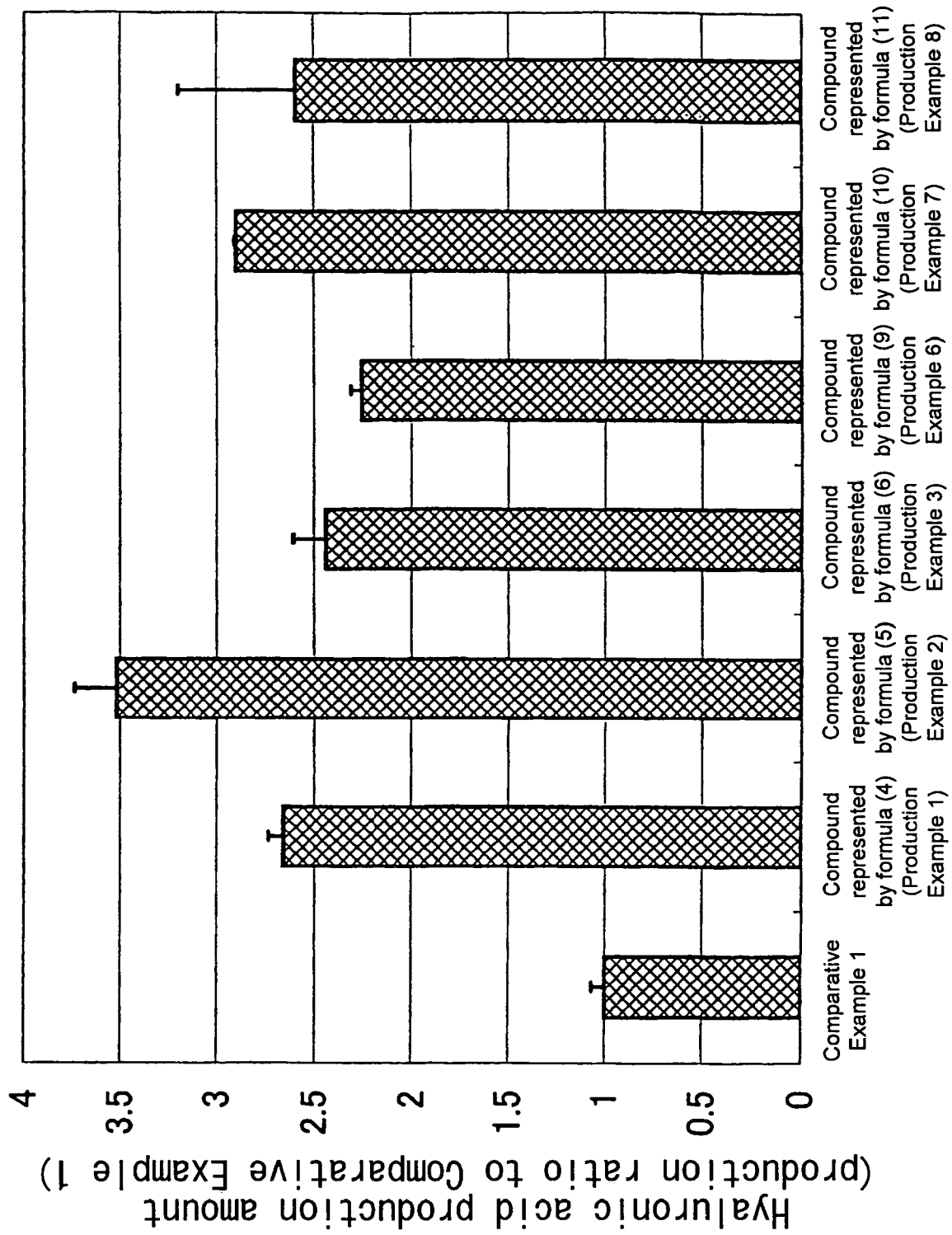
FIG. 1 is a diagram showing the result of a hyaluronic acid-production promoting test (Test Example 1) in epidermal cells using compounds produced in Production Examples 1 to 3 and 6 to 8.

An N-acetylglucosamine derivative to be used in the present invention is represented by the following formula (1) or formula (16):

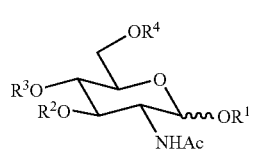

formula (1)

wherein $R^1$ is a hydrogen atom or an alkyl group having 2 to 18 carbon atoms; $R^2$, $R^3$, and $R^4$ are hydrogen atoms or acyl groups having 2 to 18 carbon atoms and may be all the same or different from others; the steric structure at position 1 may be α or β; and provided that $R^1$, $R^2$, $R^3$, and $R^4$ must not be all hydrogen atoms:

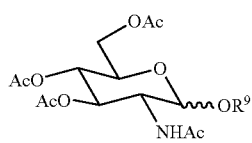

formula (16)

wherein $R^9$ denotes an acyl group having 2 to 16 carbon atoms and the steric structure at position 1 may be α or β.

In this case, $R^1$ is a hydrogen atom or a straight-chain or branched alkyl group having 2 to 18 carbon atoms, preferably 4 to 16 carbon atoms, and most preferably 8 to 12 carbon atoms and may be saturated or unsaturated. $R^2$, $R^3$, and $R^4$ are hydrogen atoms or straight-chain or branched acyl groups having 2 to 18 carbon atoms and may be all the same or different from others and preferably all hydrogen atoms or acetyl groups. The steric structure at position 1 of the pyranose ring may be α or β. However, $R^1$, $R^2$, $R^3$, and $R^4$ must not be all hydrogen atoms.

The N-acetylglucosamine derivative represented by the above-mentioned formula (1) is preferably those which can be represented by the following formula (2) or (3):

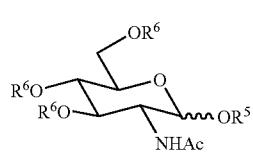

formula (2)

wherein $R^5$ is an alkyl group having 2 to 18 carbon atoms; $R^6$ is a hydrogen atom or an acetyl group; and the steric structure at position 1 may be α or β; and

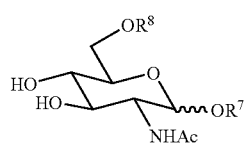

formula (3)

wherein $R^7$ is a hydrogen atom or an alkyl group having 2 to 18 carbon atoms; $R^8$ is an acyl group having 2 to 18 carbon atoms; and the steric structure at position 1 may be α or β.

In this case, $R^5$ is a straight-chain or branched alkyl group having 2 to 18 carbon atoms, preferably 4 to 16 carbon atoms, and most preferably 8 to 12 carbon atoms and may be saturated or unsaturated. $R^6$ is a hydrogen atom or an acetyl group, preferably all being hydrogen atoms or acetyl groups. $R^7$ is a hydrogen atom or a straight-chain or branched alkyl group having 2 to 18 carbon atoms, preferably 4 to 16 carbon atoms, and most preferably 8 to 12 carbon atoms and may be saturated or unsaturated. $R^8$ is a straight-chain or branched acyl group having 2 to 18 carbon atoms, preferably 6 to 16 carbon atoms, most preferably 8 to 12 carbon atoms and may be saturated or unsaturated. $R^9$ is a straight-chain or branched acyl group having 2 to 16 carbon atoms, preferably 2 to 8 carbon atoms, most preferably 2 to 4 carbon atoms.

Further, in formulas (1) to (17), the steric structure at position 1 of the pyranose ring illustrated with the wavy line part may be α or β and their mixture may be used without causing any problem.

Particular examples of the N-acetylglucosamine derivative represented by the above-mentioned general formula (2) or (3) may be those represented by the following formulae (4) to (15):

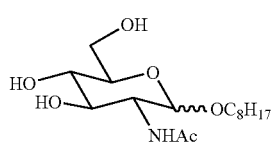

formula (4)

wherein the steric structure at position 1 may be α or β;

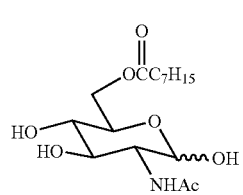

formula (5)

wherein the steric structure at position 1 may be α or β;

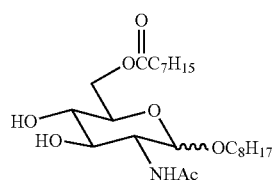

formula (6)

wherein the steric structure at position 1 may be α or β;

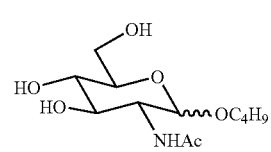

formula (7)

wherein the steric structure at position 1 may be α or β;

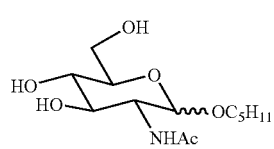

formula (8)

wherein the steric structure at position 1 may be α or β;

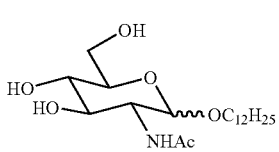

formula (9)

wherein the steric structure at position 1 may be α or β;

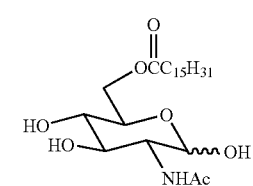

formula (10)

wherein the steric structure at position 1 may be α or β;

formula (11)

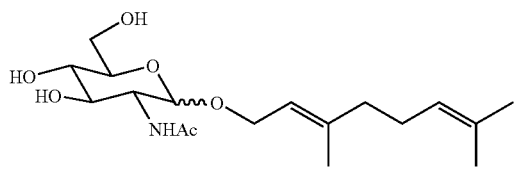

wherein the steric structure at position 1 may be α or β;

These compounds can be synthesized using a known glycosylation reaction. The outline of an exemplary synthesis method is as follows. In the case of a compound represented by formula (2) wherein $R^6$ is a hydrogen atom, a mixture of α- and β-glycosides can be produced by glycosylation of an alcohol with N-acetylglucosamine in the presence of an acid catalyst, and the α and β can be separated by using a silica gel column. Further, β-glycoside can be produced as a single compound by using oxazoline synthesis method. The compound represented by formula (3) can be produced by heating and dissolving N-acetylglucosamine or the compound represented by formula (2) in a solvent, adding a variety of fatty acid halides or anhydrides, and optionally a catalyst, and then carrying out the reaction.

The compounds represented by formulas (12) to (15) will be explained below:

Formula (12)

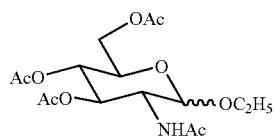

wherein the steric structure at position 1 may be α or β;

formula (13)

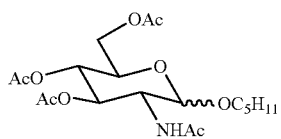

wherein the steric structure at position 1 may be α or β;

formula (14)

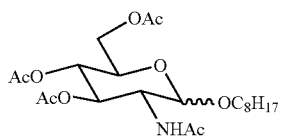

wherein the steric structure at position 1 may be α or β; and formula (15)

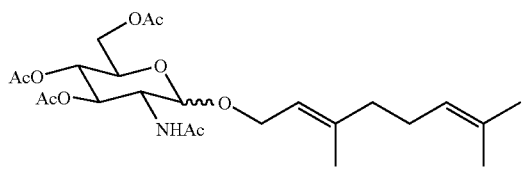

wherein the steric structure at position 1 may be α or β.

These compounds are commercially available 2-acetamide-1,3,4,6-tetra-O-acetyl-2-deoxy-β-D-glucopyranoside [the compound represented by the formula (17)] or can be produced from this compound by derivatization using glycosylation reaction according to known oxazoline synthesis methods.

Particular examples of the N-acetylglucosamine derivative represented by the formula (16) include those which can be represented by the following formula (17):

formula (17)

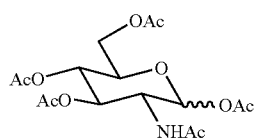

wherein the steric structure at position 1 may be α or β.

The formulation amount of the N-acetylglucosamine derivative in a hyaluronic acid production-promoting agent and a skin external preparation is preferably 0.00001 to 5.0% by mass, more preferably 0.001 to 3.0% by mass, and most preferably 0.01 to 1.0% by mass on the basis of the total weight of the composition. If it is within the range, the aimed effect of the invention can sufficiently be exhibited.

The hyaluronic acid production-promoting agent and the skin external preparation of the present invention may be in a variety of application forms such as an ointment, lotion, emulsion, milk, cataplasm, pack, mist, foam, granule, powder, gel or the like. In the present invention, the skin external preparation is a preparation to be applied for external use to any skin of the body including the scalp and includes a bath agent. The base is not particularly limited as long as it is a base to be commonly used for external application. The final form of the agent may be cosmetics, pharmaceuticals, and quasi drugs.

The hyaluronic acid production-promoting agent and the skin external preparation of the present invention may suitably contain the following additives without departing from the scope of attaining the object of the present invention, in addition to those described above: tar type color additives; silicone oils such as dimethylpolysiloxane, methylphenylpolysiloxane, and cyclic silicone; carotenoid type coloring elements such as lutein, astaxanthin and fucoxanthin; coloring pigments such as iron oxide; preservatives such as parabens and phenoxyethanol; hydrocarbons such as paraffin and vaseline; vegetable oils such as olive squalane, rice squalane, rice germ glycerides, jojoba oil, castor oil, safflower oil, olive oil, macadamia nut oil, and sunflower oil; waxes such as beeswax, Japan wax (Rhus succedanea fruit wax), and carnauba wax; ester oils such as octyldodecyl myristate, cetyl palmitate, isostearyl isostearate, and isopropyl myristate; lower alcohols such as ethanol; higher alcohols such as cetanol, behenyl alcohol, stearyl alcohol, and a branched long chain aliphatic alcohol; sterols and their derivatives such as cholesterol, phytosterol, branched fatty acid cholesterol ester, and macadamia nut fatty acid phytosteryl ester; processed oils such as hydrogenated oil; higher fatty acids such as stearic acid, myristic acid, isostearic acid, oleic acid, iso-type long chain fatty acid, and anteiso long chain fatty acid; terpenes such as limonene and hydrogenated bisabolol; triglycerides such as glyceryl tricaprylcaprate, glyceryl 2-ethylhexanoate, glyceryl triiso-type long chain fatty acid ester, and glyceryl tripalmitate; anionic surfactants such as sodium cetylsulfate and N-stearoyl-L-glutamic acid salt; nonionic surfactants such as polyoxyethylene alkyl ether, polyoxyethylene fatty acid ester, polyoxyethylene polyhydric alcohol fatty acid ester, polyoxyethylene hydrogenated castor oil, polyhydric alcohol fatty acid ester, modified silicone such as polyoxyethylene-modified silicone, polyglycerin fatty acid ester, and sucrose ester; cationic surfactants such as tetraalkylammonium salt; amphoteric surfactants such as betaine type, sulfobetaine type, and sulfoamino-acid surfactants; natural type surfactants such as lecithin, lysophosphatidylcholine, ceramide, and cerebroside; pigments such as titanium oxide and zinc oxide; antioxidants such as dibutylhydroxytoluene; inorganic salts such as sodium chloride, magnesium chloride, sodium sulfate, potassium nitrate, sodium sulfate, sodium metasilicate, and calcium chloride; organic acids and their salts such as sodium citrate, potassium acetate, sodium succinate, sodium asparaginate, sodium lactate, dichloroacetic acid, mevalonic acid, and glycyrrhizinic acid; organic amines and their salts such as ethanol amine hydrochloride, ammonium nitrate, arginine hydrochloride, diisopropylamine salt, urea, and decarboxycarnosine; chelating agents such as edetic acid; thickeners such as xanthane gum, carboxyvinyl polymer, carrageenan, pectin, alkyl-modified carboxyvinyl polymer, and agar; neutralizing agents such as potassium hydroxide, diisopropanolamine, and triethanolamine; ultraviolet absorbents such as hydroxymethoxybenzophenonesulfonate salt; polyhydric alcohols such as dipropylene glycol, marvitol, 1,3-butylene glycol, glycerin, propylene glycol, sorbitol, diglycerin, and raffinose; vitamins such as various amino acids, ascorbic acid, biotin, and tocopherol; and vitamin derivatives such as ascorbic acid sulfate ester salt, ascorbic acid phosphate ester salt, and tocopherol nicotinate.

Further, by suitably formulating the following additives to the extent without departing from the scope of attaining the object of the invention, the long-lasting effects of keeping the skin vital and moist and the higher anti-wrinkle effects are obtained: dermal hyaluronic acid production-promoting agents such as N-methyl-L-serine and yeast extract; hyaluronic acid decomposition suppressing agents such as *Naematoloma sublteritium* extract, *Boletopsis leucomelas* extract, Mokkin (*Hibiscus syviacus*) extract, *Uncaria gambir* extract, and *Eugenia caryophyllus* flower extract; differentiation promoters of keratinocytes such as diisopropylamine dichloroacetate, niacin, mevalonic acid, hot spring water, sodium metasilicate, and homogenized fruit; and barrier strengthening agents such as β-hydroxy-γ-aminobutyric acid and mevalonic acid.

EXAMPLES

The present invention will be illustrated below in more detail by the following examples. However, the invention is not by anyway to be limited to the following examples.

(1) Production Examples of N-acetylglucosamine Derivative

Production Example 1

Production of octyl(2-acetamido-2-deoxy)β-D-glucopyranoside [the compound represented by the formula (4)]

After 2 g of 2-acetamido-1,3,4,6-tetra-O-acetyl-2-deoxy-β-D-glucopyranoside was dissolved in 20 mL of anhydrous chloroform, 1.0 mL of trimethylsilyl trifluoromethanesulfonate was added and the mixture was stirred at room temperature for 5 hours. Chloroform was added to the reaction mixture, and after washing with an aqueous saturated sodium hydrogen carbonate solution, the chloroform layer was dried over anhydrous magnesium sulfate and the solvent was distilled off under reduced pressure. The residue was dissolved in 15 mL of dichloroethane, and 0.89 mL of 1-octanol and 119 mg of (±)-camphor-10-sulfonic acid were added. The mixture was stirred at 60° C. for 2 hours. Chloroform was added to the reaction mixture, and after washing with an aqueous saturated sodium hydrogen carbonate solution, the chloroform layer was dried over anhydrous magnesium sulfate, and the solvent was distilled off under reduced pressure. Finally, the resulting residue was subjected to silica gel column chromatography (elution solvent; n-hexane:ethyl acetate=2:3) to isolate a purified material. The obtained material was dissolved in a mixed solvent of 10 mL of methanol and 5 mL of 1,4-dioxane and a catalytic amount of 28% sodium methylate-methanol solution was added, and the mixture was stirred at room temperature for 1 hour. After the reaction mixture was neutralized, the solvent was distilled off. Finally, the resulting residue was crystallized from water to obtain 840 mg of octyl(2-acetamido-2-deoxy)β-D-glucopyranoside as a white crystal.

$^1$H-NMR measurement results of octyl(2-acetamido-2-deoxy)β-D-glucopyranoside are as follows:
NMR(DMSO-$d_6$)δ: 0.85(t, 3H, J=6.6 Hz), 1.23 (s, 10H), 1.40-1.45 (m, 2H), 1.77 (s, 3H), 3.00-3.10 (m, 2H), 3.20-3.50 (m, 4H), 3.65-3.75 (m, 2H), 4.25 (d, 1H, J=8.3 Hz), 4.40(t, 1H), 4.78 (d, 1H), 4.87 (d, 1H), 7.58 (d, 1H, J=8.7 Hz).

Production Example 2

Production of 2-acetamido-2-deoxy-6-O-octanoyl-α-D-glucopyranose [the compound represented by the formula (5)]

To 0.5 g of N-acetylglucosamine, 5 mL of pyridine and 5 mL of N,N-dimethylformamide were added, and the mixture was heated to 70° C. under stirring, and 0.46 mL of n-octanoyl chloride was dropwise added, and the reaction was carried out for 4 hours. On completion of the reaction, the reaction was extracted with ethyl acetate and washed with 2 mol/L hydrochloric acid, and the obtained ethyl acetate layer was dried over anhydrous magnesium sulfate and then the solvent was distilled off under reduced pressure. The resulting residue was purified by silica gel column chromatography (elution solvent; chloroform:methanol=15:1) to obtain 170 mg of 2-acetamido-2-deoxy-6-O-octanoyl-α-D-glucopyranose as a white crystal.

$^1$H-NMR measurement results of 2-acetamido-2-deoxy-6-O-octanoyl-α-D-glucopyranose are as follows:
NMR (DMSO-$d_6$) δ: 0.92 (t, 3H, J=6.8 Hz), 1.33 (s, 10H), 1.55-1.60 (m, 2H), 1.89 (s, 3H), 2.34 (t, 2H), 3.15-3.20 (m, 1H), 3.55-3.60 (m, 1H), 3.65-3.70 (m, 1H), 3.85-3.90 (m, 1H), 4.08 (dd, 1H, J=6.0, 11.6 Hz), 4.35 (dd, 1H, J=2.1, 11.8 Hz), 4.70 (d, 1H, J=5.4 Hz), 4.96 (t, 1H, J=3.5, 4.3 Hz), 5.13 (d, 1H, J=5.8 Hz), 6.54 (d, 1H, J=4.7H), 7.61 (d, 1H, J=8.1 Hz).

Production Example 3

Production of octyl(2-acetamido-2-deoxy-6-O-octanoyl)β-D-glucopyranoside [the compound represented by the formula (6)]

In 1 mL of pyridine, 100 mg of the compound [the formula (4)] obtained in Production Example 1 was dissolved, and 61 μL of n-octanoyl chloride was dropwise added, and the reaction was carried out for 4 hours. On completion of the reaction, after extracting with chloroform and washing with 2 mol/L hydrochloric acid, the ethyl acetate layer was dried over anhydrous magnesium sulfate and then the solvent was distilled off under reduced pressure. The resulting residue was purified by silica gel column chromatography (elution solvent; chloroform:methanol=20:1) to obtain 40 mg of octyl (2-acetamido-2-deoxy-6-O-octanoyl)β-D-glucopyranoside as a white crystal.

$^1$H-NMR measurement results of octyl(2-acetamido-2-deoxy-6-O-octanoyl)β-D-glucopyranoside are as follows:

NMR (DMSO-$d_6$) δ: 0.85 (t, 3H, J=6.8 Hz), 1.23(s, 18H), 1.40-1.45 (m, 2H), 1.50-1.55 (m, 2H), 1.78 (s, 3H), 2.28 (t, 2H), 3.05-3.10 (m, 1H), 3.25-3.40 (m, 4H), 3.60-3.65 (m, 1H), 4.05 (dd, 1H, J=7.2, 11.6 Hz), 4.28 (d, 1H, J=8.0 Hz), 4.30 (dd, 1H, J=1.6, 11.6 Hz), 4.90 (d, 1H, J=4.8 Hz), 5.12 (d, 1H, J=5.2 Hz), 7.61 (d, 1H, J=8.4 Hz).

Production Example 4

Production of butyl(2-acetamido-2-deoxy)β-D-glucopyranoside [the compound represented by the formula (7)]

The same reaction was carried out as that of the Production example 1, except that 1-butanol was used in place of 1-octanol to obtain 280 mg of butyl(2-acetamido-2-deoxy)β-D-glucopyranoside as a white crystal.

$^1$H-NMR measurement results of butyl(2-acetamido-2-deoxy)β-D-glucopyranoside are as follows:

NMR (DMSO-$d_6$) δ: 0.83 (t, 3H, J=7.1 Hz), 1.20-1.30 (m, 2H), 1.40-1.50 (m, 2H), 1.78 (s, 3H), 3.00-3.05 (m, 2H), 3.25-3.45 (m, 4H), 3.65-3.70 (m, 2H), 4.26 (d, 1H, J=8.0 Hz), 4.39 (t, 1H, J=5.8 Hz), 4.77 (d, 1H, J=5.0 Hz), 4.86 (d, 1H, J=4.4 Hz), 7.57 (d, 1H, J=8.7 Hz).

Production Example 5

Production of pentyl(2-acetamido-2-deoxy)β-D-glucopyranoside [the compound represented by the formula (8)]

The same reaction was carried out as that of the Production Example 1, except that 1-pentanol was used in place of 1-octanol to obtain 150 mg of pentyl(2-acetamido-2-deoxy)β-D-glucopyranoside as a white crystal.

$^1$H-NMR measurement results of pentyl(2-acetamido-2-deoxy)β-D-glucopyranoside are as follows:

NMR (DMSO-$d_6$) δ: 0.85 (t, 3H, J=6.0 Hz), 1.20-1.25 (m, 4H), 1.40-1.45 (m, 2H), 1.78 (s, 3H), 3.05-3.10 (m, 2H), 3.20-3.45 (m, 4H), 3.65-3.75 (m, 2H), 4.26 (d, 1H, J=8.0 Hz), 4.40 (t, 1H, J=6.0 Hz), 4.78 (d, 1H, J=4.8 Hz), 4.87 (d, 1H), 7.58 (d, 1H, J=8.8 Hz)

Production Example 6

Production of lauryl(2-acetamido-2-deoxy)β-D-glucopyranoside [the compound represented by formula (9)]

The same reaction was carried out as that of the Production example 1, except that 1-dodecanol was used in place of 1-octanol to obtain 450 mg of lauryl(2-acetamido-2-deoxy) β-D-glucopyranoside as a white crystal.

$^1$H-NMR measurement results of lauryl(2-acetamido-2-deoxy)β-D-glucopyranoside are as follows:

NMR (DMSO-$d_6$) δ: 0.85 (t, 3H, J=6.0 Hz), 1.23 (s, 18H), 1.40-1.45 (m, 2H), 1.84 (s, 3H), 3.00-3.10 (m, 2H), 3.20-3.50 (m, 4H), 3.65-3.75 (m, 2H), 4.25 (d, 1H, J=8.0 Hz), 4.40 (t, 1H, J=5.6 Hz), 4.79 (d, 1H, J=5.2 Hz), 4.85 (d, 1H, J=4.4 Hz)), 7.08 (d, 1H, J=8.8 Hz).

Production Example 7

Production of 2-acetamido-2-deoxy-6-O-palmitoyl-α-D-glucopyranose [the compound represented by formula (10)]

To 1 g of N-acetylglucosamine, 5 mL of pyridine and 15 mL of N,N-dimethylformamide were added, and the mixture was heated to 70° C. under stirring and 1.37 mL of palmitoyl chloride was dropwise added, and the reaction was carried out for 4 hours. On completion of the reaction, after extracting with ethyl acetate and washing with 2 mol/L hydrochloric acid, the ethyl acetate layer was dried over anhydrous magnesium sulfate and then the solvent was distilled off under reduced pressure. The resulting residue was purified by silica gel column chromatography (elution solvent; chloroform:methanol=15:1) to obtain 710 mg of 2-acetamido-2-deoxy-6-O-palmitoyl-α-D-glucopyranose as a white crystal.

$^1$H-NMR measurement results of 2-acetamido-2-deoxy-6-O-palmitoyl-α-D-glucopyranose are as follows:

NMR (DMSO-$d_6$) δ: 0.85 (t, 3H, J=6.5 Hz), 1.25 (s, 24H), 1.45-1.55 (m, 2H), 1.82 (s, 3H), 2.30 (t, 2H), 3.05-3.15 (m, 1H), 3.45-3.65 (m, 2H), 3.75-3.85 (m, 1H), 4.00 (dd, 1H, J=5.7, 11.8 Hz), 4.28 (dd, 1H, J=2.0, 11.8 Hz), 4.65 (d, 1H, J=5.7 Hz), 4.90 (t, 1H, J=3.7, 4.1 Hz), 5.07 (d, 1H, J=5.7 Hz), 6.45 (d, 1H, J=4.5H), 7.55 (d, 1H, J=8.1 Hz).

Production Example 8

Production of geranyl(2-acetamido-2-deoxy)β-D-glucopyranoside [the compound represented by formula (11)]:

The same reaction was carried out as that of the Production Example 1, except that geraniol was used in place of 1-octanol to obtain 890 mg of geranyl(2-acetamido-2-deoxy)β-D-glucopyranoside as a white crystal.

$^1$H-NMR measurement results of geranyl(2-acetamido-2-deoxy)β-D-glucopyranoside are as follows:

NMR(DMSO-$d_6$) δ: 1.57, 1.60, 1.65 (3s, 9H), 1.79(s, 3H), 1.95-2.05 (m, 4H), 3.05-3.10 (m, 2H), 3.30-3.40 (m, 2H), 3.47(dt, 1H, J=5.2, 12.0 Hz), 3.68 (dd, 1H, J=5.6, 11.6 Hz), 4.02 (dd, 1H, J=7.2, 12.0 Hz), 4.17(dd, 1H, J=5.2 Hz), 4.87(d, 1H), 5. 05-5.10 (m, 1H), 5.21 (t, 1H, J=6.4 Hz), 7.59(d, 1H, J=8.8 Hz).

Production Example 9

Production of ethyl(2-acetamido-3,4,6-tri-O-acetyl-2-deoxy)β-D-glucopyranoside [the Compound Represented by Formula (12)]

After 1 g of 2-acetamido-1,3,4,6-tetra-O-acetyl-2-deoxy-β-D-glucopyranoside [the compound represented by formula (17)] was dissolved in 10 mL of anhydrous chloroform, 0.5 mL of trimethylsilyl trifluoromethanesulfonate was added, and the mixture was stirred at room temperature for 5 hours. Chloroform was added to the reaction mixture, and after washing with an aqueous saturated sodium hydrogen carbonate solution, the chloroform layer was dried over anhydrous magnesium sulfate and then the solvent was distilled off under reduced pressure. The residue was dissolved in 8 mL of dichloroethane, and 0.17 mL of ethanol and 60 mg of (±)-camphor-10-sulfonic acid were added, and the mixture was stirred at 60° C. for 2 hours. Chloroform was added to the reaction mixture, and after washing with an aqueous saturated sodium hydrogen carbonate solution, the chloroform layer was dried over anhydrous magnesium sulfate and the solvent was distilled off under reduced pressure. Finally, the resulting residue was crystallized by using ether and n-hexane to obtain 0.5 g of ethyl(2-acetamido-3,4,6-tri-O-acetyl-2-deoxy)β-D-glucopyranoside as a white solid.

$^1$H-NMR measurement results of ethyl(2-acetamido-3,4,6-tri-O-acetyl-2-deoxy)β-D-glucopyranoside are as follows:

NMR (CDCl$_3$) δ: 1.18 (t, 3H, J=7.3 Hz), 1.93, 2.00, 2.05 (4s, 12H), 3.56 (m, 1H), 3.68 (m, 1H), 3.78 (dt, 1H, J=8.4, 8.8, 10.4 Hz), 3.88 (m, 1H), 4.12 (dd, 1H, J=2.4, 14 Hz), 4.25 (dd, 1H, J=4.8, 12.4 Hz), 4.69 (d, 1H, J=8.4 Hz), 5.03 (t, 1H, J=9.6 Hz), 5.30 (t, 1H, J=9.2 Hz), 5.43 (d, 1H, J=8.8 Hz).

Production Example 10

Production of pentyl(2-acetamido-3,4,6-tri-O-acetyl-2-deoxy)β-D-glucopyranoside [the Compound Represented by Formula (13)]

After 1.5 g of 2-acetamido-1,3,4,6-tetra-O-acetyl-2-deoxy-β-D-glucopyranoside was dissolved in 15 mL of anhydrous chloroform, 0.75 mL of trimethylsilyl trifluoromethanesulfonate was added, and the mixture was stirred at room temperature for 5 hours. Chloroform was added to the reaction mixture, and after washing with an aqueous saturated sodium hydrogen carbonate solution, the chloroform layer was dried over anhydrous magnesium sulfate and then the solvent was distilled off under reduced pressure. The residue was dissolved in 15 mL of dichloroethane and 0.51 mL of n-amyl alcohol and 99 mg of (±)-camphor-10-sulfonic acid were added thereto and the mixture was stirred at 60° C. for 2 hours. Chloroform was added to the reaction mixture, and after washing with an aqueous saturated sodium hydrogen carbonate solution, the chloroform layer was dried over anhydrous magnesium sulfate and the solvent was distilled off under reduced pressure. Finally, the resulting residue was subjected to silica gel column chromatography (elution solvent; n-hexane:ethyl acetate=2:3) to isolate and purify 1.1 g of pentyl(2-acetamido-3,4,6-tri-O-acetyl-2-deoxy)β-D-glucopyranoside as a white solid.

$^1$H-NMR measurement results of pentyl(2-acetamido-3,4,6-tri-O-acetyl-2-deoxy)β-D-glucopyranoside are as follows:

NMR (CDCl$_3$) δ: 0.87 (t, 3H, J=6.2 Hz), 1.28 (s, 4H), 1.50-1.55 (m, 2H), 2.00, 2.03, 2.14 (4s, 12H), 3.45 (dt, 1H, J=7.2, 9.2 Hz), 3.65-3.70 (m, 1H), 3.75-3.85 (m, 2H), 4.13 (dd, 1H, J=2.4, 12.4 Hz), 4.25 (dd, 1H, J=4.8, 12.4 Hz), 4.66 (d, 1H, J=8.0 Hz), 5.03 (t, 1H, J=9.6 Hz), 5.29 (t, 1H, J=9.2 Hz), 5.40 (d, 1H, J=8.8 Hz).

Production Example 11

Production of octyl(2-acetamido-3,4,6-tri-O-acetyl-2-deoxy)β-D-glucopyranoside [the Compound Represented by Formula (14)]

After 2 g of 2-acetamido-1,3,4,6-tetra-O-acetyl-2-deoxy-β-D-glucopyranoside was dissolved in 20 mL of anhydrous chloroform, 1.0 mL of trimethylsilyl trifluoromethanesulfonate was added thereto and the mixture was stirred at room temperature for 5 hours. Chloroform was added to the reaction mixture, and after washing with an aqueous saturated sodium hydrogen carbonate solution, the chloroform layer was dried over anhydrous magnesium sulfate and then the solvent was distilled off under reduced pressure. The residue was dissolved in 15 mL of dichloroethane, and 0.89 mL of n-octanol and 119 mg of (±)-camphor-10-sulfonic acid were added, and the mixture was stirred at 60° C. for 2 hours. Chloroform was added to the reaction mixture, and after washing with an aqueous saturated sodium hydrogen carbonate solution, the chloroform layer was dried over anhydrous magnesium sulfate and the solvent was distilled off under reduced pressure. Finally, the resulting residue was subjected to silica gel column chromatography (elution solvent; n-hexane:ethyl acetate=2:3) to isolate and purify to obtain 1.5 g of octyl(2-acetamido-3,4,6-tri-O-acetyl-2-deoxy)β-D-glucopyranoside as a white solid.

$^1$H-NMR measurement results of octyl(2-acetamido-3,4,6-tri-O-acetyl-2-deoxy)β-D-glucopyranoside are as follows:

NMR (CDCl$_3$) δ: 0.86 (t, 3H, J=6.2 Hz), 1.25 (s, 10H), 1.50-1.55 (m, 2H), 1.92, 1.99, 2.00, 2.05 (4s, 12H), 3.40-3.45 (m, 1H), 3.65-3.70 (m, 1H), 3.75-3.90 (m, 2H), 4.10 (d, 1H, J=12.2 Hz), 4.23 (d, 1H, J=4.8, 12.2 Hz), 4.65 (d, 1H, J=8.3 Hz), 5.03 (t, 1H, J=9.8 Hz), 5.28 (t, 1H, J=9.8 Hz), 5.41 (d, 1H, J=8.7 Hz).

Production Example 12

Production of geranyl(2-acetamido-3,4,6-tri-O-acetyl-2-deoxy)β-D-glucopyranoside [the Compound Represented by Formula (15)]

After 5 g of 2-acetamido-1,3,4,6-tetra-O-acetyl-2-deoxy-β-D-glucopyranoside was dissolved in 50 mL of anhydrous chloroform, 2.6 mL of trimethylsilyl trifluoromethanesulfonate was added, and the mixture was stirred at room temperature for 5 hours. Chloroform was added to the reaction mixture, and after washing with an aqueous saturated sodium hydrogen carbonate solution, the chloroform layer was dried over anhydrous magnesium sulfate and the solvent was distilled off under reduced pressure. The residue was dissolved in 20 mL of dichloroethane, and 2.5 mL of geraniol and 298 mg of (±)-camphor-10-sulfonic acid were added and the mixture was stirred at 60° C. for 2 hours. Chloroform was added to the reaction mixture, and after washing with an aqueous saturated sodium hydrogen carbonate solution, the chloroform layer was dried over anhydrous magnesium sulfate and the solvent was distilled off under reduced pressure. Finally, the resulting residue was subjected to silica gel column chromatography (elution solvent; n-hexane:ethyl acetate=2:3) to isolate and purify to obtain 4.3 g of geranyl (2-acetamido-3,4,6-tri-O-acetyl-2-deoxy)β-D-glucopyranoside as a white solid.

$^1$H-NMR measurement results of geranyl(2-acetamido-3,4,6-tri-O-acetyl-2-deoxy)β-D-glucopyranoside are as follows:

NMR (CDCl$_3$) δ: 1.59, 1.64, 1.67 (3s, 9H), 1.91 (s, 3H), 1.99, 2.00, 2.05 (3s, 9H), 3.60-3.65 (m, 1H), 3.78 (dt, 1H, J=2.8, 12.4 Hz), 4.10-4.30 (m, 3H), 4.68 (d, 1H, J=8.8 Hz), 5.00-5.10 (m, 2H), 5.20-5.40 (m, 2H).

(2) Test Examples Using N-acetylglucosamine Derivatives

Next, Test Examples for evaluating the N-acetylglucosamine derivatives produced in the above-mentioned Production Examples of the invention will be described.

Test Example 1 (Test for Hyaluronic Acid Production Promotion in Normal Human Epidermal Cells)

Normal human epidermal cells (manufactured by Kurabo Industries Ltd.) were inoculated into 24-well plates and cultured in a culture medium for proliferation to the confluent density. Then N-acetylglucosamine derivatives produced in the above-mentioned Production Examples 1 to 3 and 6 to 8 were added to a final concentration of 50 μmol/L (25 μmol/L, only for the derivative obtained in Production Example 7), and N-acetylglucosamine derivatives produced in the Production Examples 4 and 5 were added to a final concentration of 1 mmol/L. After 48-hour culture from the addition, the hyaluronic acid released to the culture medium was measured. The measurement of the hyaluronic acid was carried out by using a commercially available hyaluronic acid measurement kit (manufactured by Chugai Pharmaceutical Co., Ltd.).

The amount of hyaluronic acid produced by dermal fibroblast cells cultured in the culture medium containing a test substance is represented as a ratio relative to the amount of hyaluronic acid produced by the cells cultured in the culture medium containing N-acetylglucosamine at a final concentration of 1 mmol/L (which is defined as 1, Comparative Example 1). The results are shown in FIG. 1 and FIG. 2.

As shown in FIG. 1, octyl(2-acetamido-2-deoxy)β-D-glucopyranoside [the compound represented by formula (4)] of Production Example 1,2-acetamido-2-deoxy-6-O-octanoyl-α-D-glucopyranose [the compound represented by formula (5)] of Production Example 2, octyl(2-acetamido-2-deoxy-6-O-octanoyl)β-D-glucopyranoside [the compound represented by formula (6)] of Production Example 3, lauryl(2-acetamido-2-deoxy)β-D-glucopyranoside [the compound represented by formula (9)] of Production Example 6,2-acetamido-2-deoxy-6-O-palmitoyl-α-D-glucopyranose [the compound represented by formula (10)] of Production Example 7, and geranyl(2-acetamido-2-deoxy)β-D-glucopyranoside [the compound represented by formula (11)] of Production Example 8 exhibited 2.5- to 3.5-higher hyaluronic acid production-promoting effect at about 1/20 concentration (about 1/40 in the case of Production Example 7) when compared with N-acetylglucosamine. Especially, the compound represented by formula (3) wherein R$^7$ is hydrogen was found having the high production-promoting activity.

Figure 2:
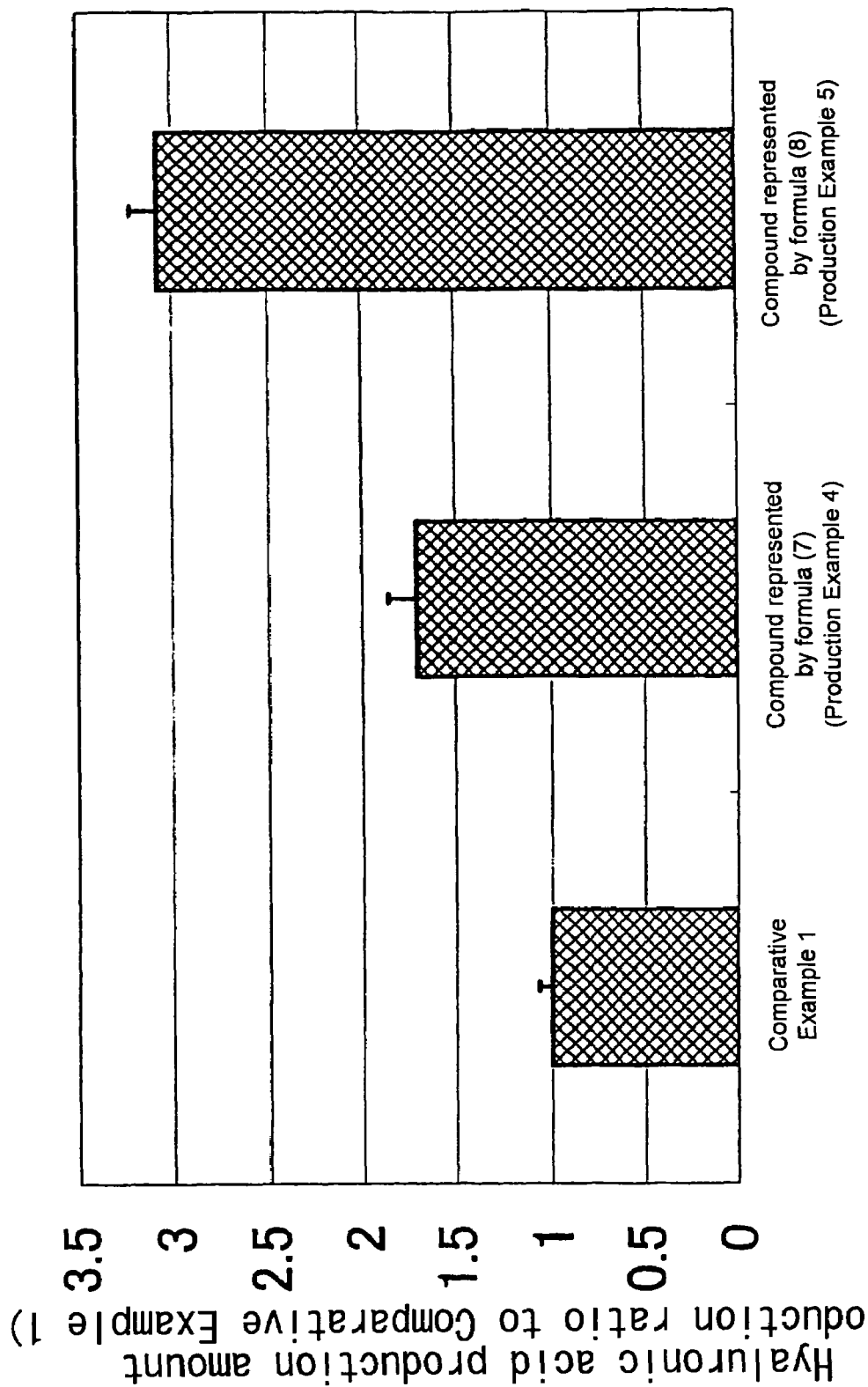
FIG. 2 is a diagram showing the result of a hyaluronic acid-production promoting test (Test Example 1) in epidermal cells using compounds produced in Production Examples 4 and 5.

Further, as shown in FIG. 2, butyl(2-acetamido-2-deoxy)β-D-glucopyranoside [the compound represented by formula (7)] of Production Example 4 and pentyl(2-acetamido-2-deoxy)β-D-glucopyranoside [the compound represented by formula (8)] of Production Example 5 exhibited 1.5- to 3-times higher hyaluronic acid production-promoting effect at the same concentration compared with N-acetylglucosamine.

Test Example 2 (Test for Hyaluronic Acid Production Promotion in Normal Human Epidermal Cells)

Normal human epidermal cells (manufactured by Kurabo Industries Ltd.) were inoculated into 24-well plates and cultured in a culture medium for proliferation to the confluent density, and then 2-acetamido-1,3,4,6-tetra-O-acetyl-2-deoxy-β-D-glucopyranoside represented by formula (17) to a final concentration of 100 μmol/L, N-acetylglucosamine derivative obtained in Production Example 9 at a final concentration of 1 mmol/L, and N-acetylglucosamine derivatives obtained in Production Examples 10 to 12 at a final concentration of 100 mmol/L were added. After 48-hour culture from the addition, the amount of hyaluronic acid released into the culture medium was measured. The measurement of the hyaluronic acid was carried out by using a commercially available hyaluronic acid measurement kit (manufactured by Chugai Pharmaceutical Co., Ltd.). The results are shown in FIG. 3.

Figure 3:
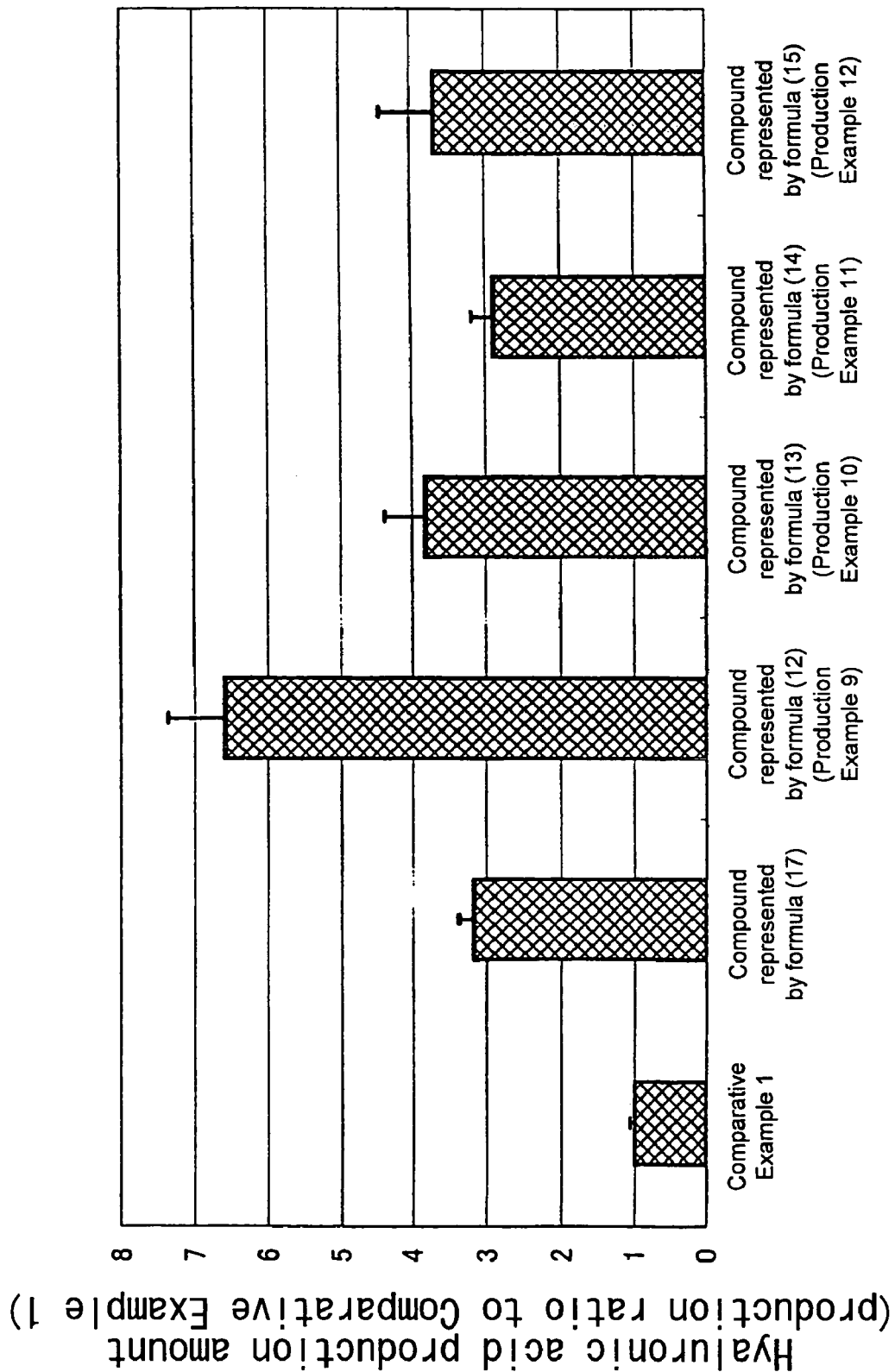
FIG. 3 is a diagram showing the result of a hyaluronic acid-production promoting test (Test Example 2) in epidermal cells using 2-acetamido-1,3,4,6-tetra-O-acetyl-2-deoxy-β-D-glucopyranoside [the compound represented by the formula (17)] produced in Production Examples 9 to 12.

As shown in FIG. 3, ethyl(2-acetamido-3,4,6-tri-O-acetyl-2-deoxy)β-D-glucopyranoside [the compound represented by formula (12)] of Production Example 9 exhibited 6.5-times higher hyaluronic acid production-promoting effect at the same concentration when compared with N-acetylglucosamine. Further, pentyl(2-acetamido-3,4,6-tri-O-acetyl-2-deoxy)β-D-glucopyranoside [the compound represented by formula (13)] of Production Example 10, octyl(2-acetamido-3,4,6-tri-O-acetyl-2-deoxy)β-D-glucopyranoside [the compound represented by formula (14)] of Production Example 11, geranyl(2-acetamido-3,4,6-tri-β-acetyl-2-deoxy)β-D-glucopyranoside [the compound represented by formula (15)] of Production Example 12, and 2-acetamido-1,3,4,6-tetra-O-acetyl-2-deoxy-β-D-glucopyranoside [the compound represented by formula (17)] exhibited 3.8-, 2.8-, 3.7-, and 3.0-times higher hyaluronic acid production-promoting effect at 1/10 concentration compared with N-acetylglucosamine, respectively.

Test Example 3 (Test for Hyaluronic Acid Production Promotion in Normal Human Dermal Fibroblast Cells)

Normal human dermal fibroblasts (manufactured by American Type Culture Collection) were inoculated into 24-well plates and cultured in a culture medium for proliferation to be confluent and then the 100 μmol/L of N-acetylglucosamine derivative in the above-mentioned Production Example 1 and 25 μmol/L of N-acetylglucosamine derivative in the Production Example 6 were added. After 48-hour culture from the addition, the amount of hyaluronic acid released into the culture medium was measured. The measurement of the hyaluronic acid was carried out by using commercially available hyaluronic acid measurement kit (manufactured by Chugai Pharmaceutical Co., Ltd.).

The amount of hyaluronic acid produced by dermal fibroblast cells cultured in the culture medium containing a test substance is represented as a ratio relative to the amount of hyaluronic acid produced by the cells in the culture medium containing N-acetylglucosamine at a final concentration of 1 mmol/L (Comparative Example 2). The results are shown in FIG. 4.

Figure 4:
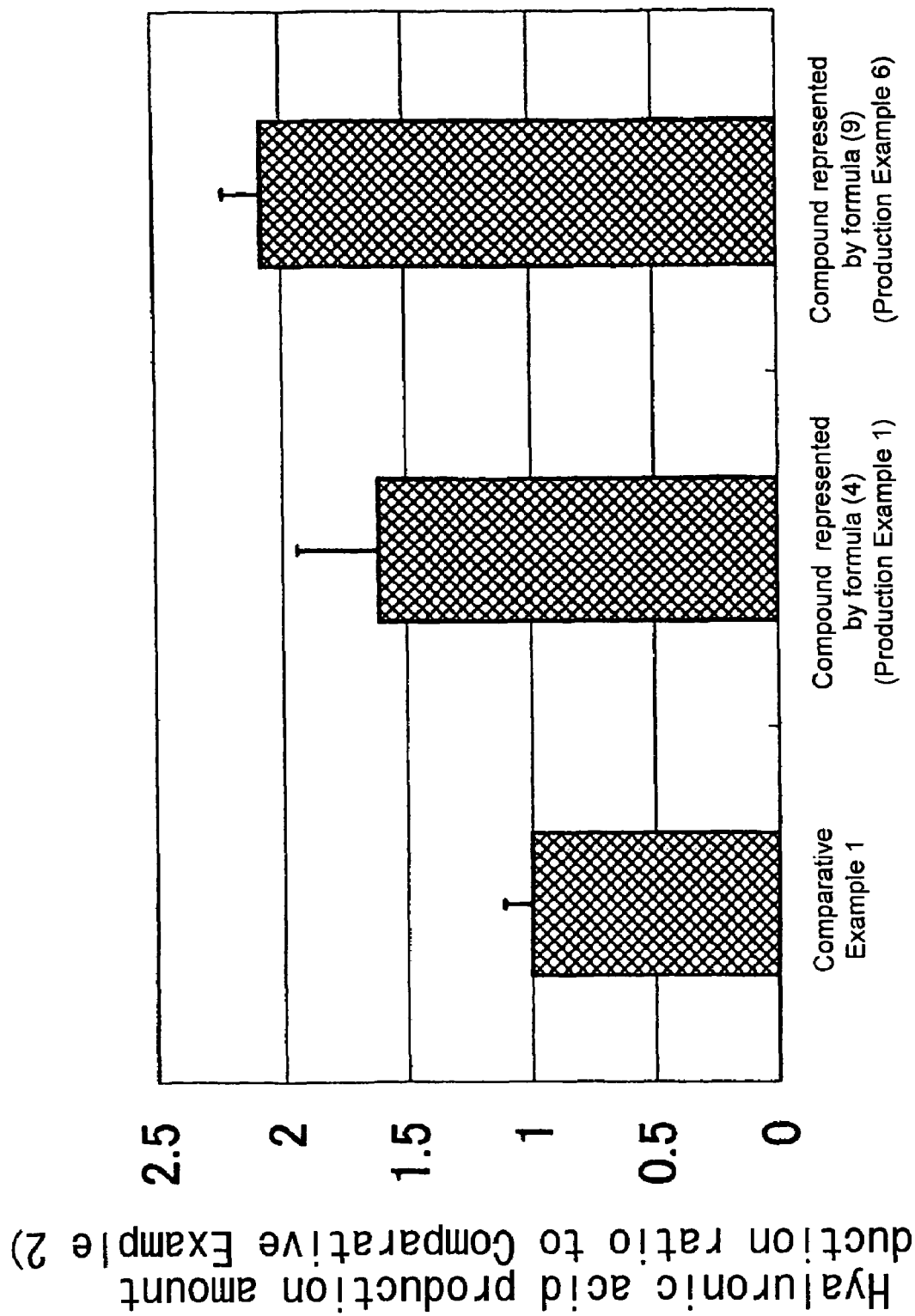
FIG. 4 is a diagram showing the result of a hyaluronic acid-production promoting test (Test Example 3) in dermal cells using compounds produced in Production Examples 1 and 6.

As shown in FIG. 4, both octyl(2-acetamido-2-deoxy)β-D-glucopyranoside [the compound represented by formula (4)] of Production Example 1 and lauryl(2-acetamido-2-deoxy)β-D-glucopyranoside [the compound represented by formula (9)] of Production Example 6 exhibited 1.5- to 2-times higher hyaluronic acid production-promoting effect at an approximately 1/10 to 1/40 concentration compared with N-acetyl-glucosamine.

Test Examples 4 to 7 and Comparative Examples 3 and 4 (Evaluation by Subjects)

Women in forties to sixties as the subjects were divided into 8 groups each consisting of 20 women. Creams with the compositions shown in Table 1 (Test Examples 4 and 5 and Comparative Example 3) and face lotions with the compositions shown in Table 2 (Test Examples 6 and 7 and Comparative Example 4) were each given to a separate group and an appropriate amount was applied to the faces of the subjects twice a day for 3 consecutive months. After successive use, the vital feeling of the skin was evaluated.

The evaluation was carried out based on the following four grades: remarkably effective (the vital feeling of the skin was considerably improved), effective (the vital feeling of the skin was well improved), slightly effective (the vital feeling of the skin was improved), and no effect (no change). The effect was determined based on the ratio (%) of the total number of the subjects who evaluated the creams or the face lotions as being remarkably effective and effective.

TABLE 1

|  | Test Example 4 | Test Example 5 | Comparative Example 3 |
|---|---|---|---|
| Compound represented by formula (4) (Production Example 1) | 0.1 | — | — |
| Compound represented by formula (17) | — | 0.1 | — |
| Stearic acid | | 2 | |
| Monostearic acid glycerin | | 2 | |
| Cetanol | | 3 | |
| Cholesterol | | 0.5 | |
| Vaseline | | 2 | |
| Squalane | | 10 | |
| Liquid paraffin | | 10 | |
| Dimethylpolysiloxane | | 1 | |
| Butylparaben | | 0.1 | |
| Methylparaben | | 0.1 | |
| Sodium N-stearoylglutamate | | 1 | |
| Glycerin dipropylene glycol | | 5 | |
| Purified water | | balance | |
| Total | | 100 | |
| Evaluation (%) | 80 | 80 | 45 |

* The contents are all based on % by mass.

TABLE 2

|  | Test Example 6 | Test Example 7 | Comparative Example 4 |
|---|---|---|---|
| Compound represented by formula (4) (Production Example 1) | 0.01 | — | — |
| Compound represented by formula (17) | — | 0.01 | — |
| Ethanol | | 10 | |
| Polyoxyethylene hydrogenated castor oil (60 E.O.) | | 1 | |
| Glycerin | | 3 | |
| 1,3-butylene glycol | | 2 | |
| Dipropylene glycol | | 3 | |
| Monopotassium phosphate | | 0.05 | |
| Dipotassium phosphate | | 0.05 | |
| Edetate disodium | | 0.05 | |
| Methylparaben | | 0.1 | |
| Purified water | | balance | |
| Total | | 100 | |
| Evaluation (%) | 55 | 55 | 30 |

* The contents are all based on % by mass.

The results shown in Table 1 and Table 2 revealed that the cosmetics using N-acetylglucosamine derivatives of the invention had the effect of improving the vital feeling of the skin.

Additionally, in any case using the cosmetics of the Test Examples, no symptoms considered to be the side effects such as red rash, inflammation, and the like were observed on the skin and thus it was made clear that the cosmetics according to the invention were excellent also in the safety.

(3) EXAMPLES

Example 1

Skin Cream

A skin cream with the following composition was prepared by a conventional method.

| Ingredients | Formulation amount (% by mass) |
|---|---|
| Beeswax | 2.0 |
| Stearic acid | 5.0 |
| Stearyl alcohol | 5.0 |
| Hydrogenated lanolin | 2.0 |
| Squalene | 20.0 |
| Sorbitan monostearate | 3.0 |
| Polyoxyethylene (20) sorbitan monostearate | 3.0 |
| Propylene glycol | 5.0 |
| Methylparaben | 0.2 |
| Compound represented by formula (4) (Production Example 1) | 0.1 |
| Purified water | Balance in the total 100 |

Example 2

Skin Cream

A skin cream with the following composition was prepared by a conventional method.

| Ingredients | Formulation amount (% by mass) |
|---|---|
| Beeswax | 2.0 |
| Stearic acid | 5.0 |
| Stearyl alcohol | 5.0 |
| Hydrogenated lanolin | 2.0 |
| Squalene | 20.0 |
| Sorbitan monostearate | 3.0 |
| Polyoxyethylene (20) sorbitan monostearate | 3.0 |
| Propylene glycol | 5.0 |
| Methylparaben | 0.2 |
| Compound represented by formula (5) (Production Example 2) | 0.5 |
| Purified water | Balance in the total 100 |

Example 3

Skin Lotion

A skin lotion with the following composition was prepared by a conventional method.

| Ingredients | Formulation amount (% by mass) |
|---|---|
| Olive oil | 10.0 |
| Isopropyl myristate | 1.0 |
| Polyoxyethylene (6) nonylphenyl ether | 0.5 |
| Propylene glycol | 1.0 |
| Glycerin | 2.0 |
| Methylparaben | 0.1 |
| Ethanol | 7.0 |
| Compound represented by formula (6) (Production Example 3) | 0.5 |
| Purified water | Balance in the total 100 |

Example 4

Skin Lotion

A skin lotion with the following composition was prepared by a conventional method.

| Ingredients | Formulation amount (% by mass) |
|---|---|
| Olive oil | 10.0 |
| Isopropyl myristate | 1.0 |
| Polyoxyethylene (6) nonylphenyl ether | 0.5 |
| Propylene glycol | 1.0 |
| Glycerin | 2.0 |
| Methylparaben | 0.1 |
| Ethanol | 7.0 |
| Compound represented by formula (8) (Production Example 5) | 1.0 |
| Purified water | Balance in the total 100 |

Example 5

Bath Agent

A bathing agent with the following composition was prepared by a conventional method.

| Ingredients | Formulation amount (% by mass) |
|---|---|
| Compound represented by formula (5) (Production Example 2) | 1.0 |
| Sodium hydrogen carbonate | balance |
| Sodium carbonate | 20.0 |
| Sodium sulfate | 15.0 |
| Sodium chloride | 7.5 |
| Silicic acid anhydride | 0.5 |
| 1,3-butylene glycol | 1.0 |
| Urea | 1.0 |
| Seaweed extract | 1.0 |
| Color additive | q.s. |
| Dextrin | q.s. |
| Fragrance | q.s. |

Examples 6 to 8

Skin Cream

Skin creams with the following compositions were prepared by a conventional method.

| Ingredients | Example 6 | Example 7 | Example 8 |
|---|---|---|---|
| Compound represented by formula (4) (Production Example 1) | 0.1 | — | — |
| Compound represented by formula (5) (Production Example 2) | — | 0.1 | — |
| Compound represented by general formula (6) (Production Example 3) | — | — | 0.1 |
| Stearic acid | 1 | 1 | — |
| Isostearic acid | — | — | 1 |
| Monostearic acid glycerin | 2 | 2 | 2 |
| Behenyl alcohol | 2 | 2 | 2 |
| Bleached beeswax | 1 | 1 | — |
| Cetyl myristate | 1 | 1 | 1 |
| Sorbitan sesquioleate | 1 | 1 | 1 |
| N-stearoylphytosphingosine | 0.1 | 0.1 | 0.1 |
| Hydrogenated lecithin | 0.1 | 0.1 | 0.1 |
| Plant squalane | 5 | 5 | 5 |
| Octyldodecyl myristate | 5 | 5 | 5 |
| Phellodendron bark extract | 0.1 | 1 | 0.1 |
| Pyracantha fortuneana fruit extract | 0.1 | 0.3 | — |
| Water-soluble glycyrrhiza extract | — | — | 0.1 |
| 1,3-butylene glycol | 5 | 10 | 5 |
| Concentrated glycerin | 5 | 5 | 5 |
| p-oxybenzoic acid ester | 0.2 | 0.2 | 0.2 |
| N-acetylglucosamine oligomer | 0.1 | 0.1 | 0.1 |
| Ascorbic acid phosphate ester magnesium salt | 0.1 | 0.1 | 0.1 |
| Ascorbic acid phosphate ester sodium salt | 0.1 | 0.1 | 0.1 |
| γ-aminobutyric acid | 0.1 | 0.1 | 0.1 |
| Sodium N-stearoylglutamate | 0.2 | 0.2 | 0.2 |
| Alkyl-modified carboxyvinyl polymer *1 | 0.05 | 0.05 | 0.05 |
| Nicotinic acid amide | 0.1 | 0.1 | 0.1 |
| Sarcosine | 0.1 | 0.1 | 0.1 |
| Purified water | balance | balance | balance |

*1: PEMULEN TR-1, manufactured by B. F. Goodrich

Examples 9 to 11

Lotion

Lotions with the following compositions were prepared by a conventional method.

| Ingredients | Example 9 | Example 10 | Example 11 |
|---|---|---|---|
| Compound represented by formula (4) (Production Example 1) | 0.1 | — | — |
| Compound represented by formula (5) (Production Example 2) | — | 0.1 | — |
| Compound represented by formula (6) (Production Example 3) | — | — | 0.1 |
| Phellodendron bark extract | 0.1 | 0.3 | 0.3 |
| Hibiscus extract | 0.2 | 0.5 | 0.5 |
| Lactic acid bacteria culture medium | 0.1 | 0.1 | 0.1 |

-continued

| Ingredients | Formulation amount (% by mass) | | |
|---|---|---|---|
| | Example 9 | Example 10 | Example 11 |
| 1,3-butylene glycol | 5 | 5 | 5 |
| Dipropylene glycol | 5 | 5 | 5 |
| Raffinose | 1 | 1 | 1 |
| Ethanol | 1 | 1 | 1 |
| Phenoxyethanol | 0.2 | 0.2 | 0.2 |
| Pectin | 0.05 | 0.05 | 0.05 |
| Xanthane gum | 0.1 | 0.1 | 0.1 |
| Sodium citrate | 0.05 | 0.05 | 0.05 |
| Equisetum arvense extract | 0.1 | 0.1 | 0.1 |
| Diisopropylamine dichloroacetic acid | 0.2 | 0.2 | 0.2 |
| γ-amino-β-hydroxybutyric acid | 0.2 | 0.2 | 0.2 |
| Sodium hyaluronate | 0.001 | 0.001 | 0.001 |
| Dipotassium glycyrrhizate | 0.2 | 0.2 | 0.2 |
| Naematoloma sublateritium extract | 0.05 | 0.05 | 0.05 |
| Decarboxycarnosine hydrochloride | 0.05 | 0.05 | 0.05 |
| Fragrance | 0.02 | 0.02 | 0.02 |
| Purified water | balance | balance | balance |

Examples 12 to 14

Gel

Gels with the following compositions were prepared by a conventional method.

| Ingredients | Formulation amount (% by mass) | | |
|---|---|---|---|
| | Example 12 | Example 13 | Example 14 |
| Compound represented by formula (4) (Production Example 1) | 0.1 | — | — |
| Compound represented by formula (5) (Production Example 2) | — | 0.1 | — |
| Compound represented by formula (6) (Production Example 3) | — | — | 0.1 |
| Decamethylcyclopentasiloxane | 10 | 10 | 10 |
| Isostearyl isostearate | 1 | — | — |
| Olive oil | — | 1 | — |
| Macadamia nut oil | — | — | 1 |
| Eucalyptus oil | 0.1 | — | 0.1 |
| Hexyldecanol | 1 | 0.1 | — |
| dl-α-tocopherol nicotinate | — | 0.1 | — |
| Polyoxyethylene (60) hydrogenated castor oil | 2 | 2 | 2 |
| Spherical silicone powder *2 | 1 | 1 | 5 |
| Phellodendron bark extract | 0.1 | 1 | 0.1 |
| Water-soluble chlorophyll | 0.02 | 0.02 | 0.02 |
| Salvia extract | — | 0.3 | 0.1 |
| 1,3-Butylene glycol | 5 | 10 | 5 |
| Sorbitol liquid | 3 | 3 | 3 |
| Polyethylene glycol 4000 | 1 | 1 | 1 |
| Carboxyvinyl polymer | 0.2 | 0.2 | 0.2 |
| Sugar ceramide *3 | 0.1 | 0.1 | 0.1 |
| p-Oxybenzoic acid ester | 0.2 | 0.2 | 0.2 |
| Mevalonolactone | 0.5 | 0.5 | 0.5 |
| Edetic acid salt | 0.02 | 0.02 | 0.02 |
| Potassium hydroxide | 0.05 | 0.05 | 0.05 |
| Purified water | balance | balance | balance |

*2: Tospearl, manufactured by GE Toshiba Silicone Co., Ltd.
*3: Bioceramide, manufactured by Kibun Food Chemical Co., Ltd.

Examples 15 to 17

Lipophilic Cream

Lipophilic creams with the following compositions were prepared by a conventional method.

| Ingredients | Formulation amount (% by mass) | | |
|---|---|---|---|
| | Example 15 | Example 16 | Example 17 |
| Compound represented by formula (4) (Production Example 1) | 0.1 | — | — |
| Compound represented by formula (5) (Production Example 2) | — | 0.1 | — |
| Compound represented by formula (6) (Production Example 3) | — | — | 0.1 |
| Co-modified silicone *4 | 2 | 2 | 2 |
| Polyoxethylene-modified silicone dispersion *5 | — | 2 | — |
| Squalane | — | — | 10 |
| Decamethylcyclopentasiloxane | 15 | 20 | 10 |
| Methylpolysiloxane | 5 | 2 | 3 |
| Cholesteryl branched long chain fatty acid ester *6 | — | — | 3 |
| Silicone elastomer dispersion *7 | 5 | 2 | — |
| Phellodendron bark extract | 1 | 1 | 1 |
| Glycyrrhiza extract | 0.1 | 0.1 | 0.1 |
| Water-soluble chlorophyll | 0.02 | 0.02 | 0.02 |
| Sodium chloride | 1 | 1 | 1 |
| Dipropylene glycol | 5 | 5 | 5 |
| Concentrated glycerin | 5 | 5 | 5 |
| Raffinose | 1 | 1 | 1 |
| p-Oxybenzoic acid ester | 0.3 | 0.3 | 0.3 |
| N-Methyl-L-serine | 0.5 | 0.5 | 0.5 |
| Purified water | balance | balance | balance |

*4: ABIL EM90, manufactured by Goldschmidt A.G.
*5: Silicone BY 22-008, manufactured by Dow Corning Toray Silicone
*6: YOFCO CLE-NH, manufactured by Nippon Fine Chemical Co., Ltd.
*7: Trefil, manufactured by Dow Corning Toray Silicone Co., Ltd.

Examples 18 to 20

Sunscreen

Sunscreens with the following compositions were prepared by a conventional method.

| Ingredients | Formulation amount (% by mass) | | |
|---|---|---|---|
| | Example 18 | Example 19 | Example 20 |
| Compound represented by formula (4) (Production Example 1) | 0.1 | — | — |
| Compound represented by formula (5) (Production Example 2) | — | 0.1 | — |
| Compound represented by formula (6) (Production Example 3) | — | — | 0.1 |
| Dioctyl ether | 10 | 10 | 10 |
| Co-modified silicone *4 | 2 | 2 | 2 |
| Glyceryl tri-2-ethylhexanoate | 5 | 5 | 5 |
| Hydrogenated oil | 0.1 | 0.1 | 0.1 |
| Methylphenylpolysiloxane | 3 | 3 | 3 |
| Phytosteryl macadamia nut fatty acid | — | — | 2 |
| 2-Ethylhexyl p-methoxycinnamate | — | 7 | 7 |
| Titanium oxide | 5 | 5 | 4 |

-continued

| Ingredients | Example 18 | Example 19 | Example 20 |
|---|---|---|---|
| Zinc oxide | 5 | 5 | 4 |
| Phellodendron bark extract | 1 | 1 | 1 |
| Magnesium chloride | 1 | 1 | 1 |
| 1,3-Butylene glycol | 5 | 5 | 5 |
| Phenoxyethanol | 0.3 | 0.3 | 0.3 |
| Hibiscus extract | 1 | 1 | 1 |
| Aloe extract | 0.1 | 0.1 | 0.1 |
| Yeast extract *8 | 1 | 1 | 1 |
| Purified water | balance | balance | balance |

*4: ABIL EM90, manufactured by Goldschmidt A. G.
*8: Dismutin, manufactured by PentaFarm Ltd.

Example 21

Face Lotion

| Ingredients | Formulation amount (% by mass) |
|---|---|
| Ethanol | 10 |
| Polyoxyethylene (60) hydrogenated castor oil | 1 |
| Glycerin | 3 |
| 1,3-Butylene glycol | 2 |
| Dipropylene glycol | 3 |
| Polyethylene glycol 1500 | 1 |
| Phosphoric acid salt | q.s. |
| Edetic acid salt | q.s. |
| Methylparaben | q.s. |
| Compound represented by formula (10) (Production Example 7) | 0.1 |
| Anti-oxidant | q.s. |
| Purified water | balance |

Examples 22 and 23

Emulsion

| Ingredients | Example 22 | Example 23 |
|---|---|---|
| Stearic acid | 1 | 1 |
| Stearic acid glycerin ester | 2 | 2 |
| Cetanol | 1 | 1 |
| Cholesterol | 0.5 | 0.5 |
| Vaseline | 2 | 2 |
| Squalane | 5 | 5 |
| Liquid paraffin | 5 | 5 |
| Silicone oil | 1 | 1 |
| Acylglutamic acid salt | 1 | 1 |
| Xanthane gum | 0.5 | 0.5 |
| Glycerin | 2 | 2 |
| Dipropylene glycol | 3 | 3 |
| Compound represented by formula (5) (Production Example 2) | 0.1 | — |
| Compound represented by formula (10) (Production Example 7) | — | 0.1 |
| Butylparaben | q.s. | q.s. |
| Anti-oxidant | q.s. | q.s. |
| Purified water | balance | balance |

Examples 24 and 25

Cream

| Ingredients | Example 24 | Example 25 |
|---|---|---|
| Stearic acid | 2 | 2 |
| Stearic acid glycerin ester | 2 | 2 |
| Cetanol | 3 | 3 |
| Cholesterol | 0.5 | 0.5 |
| Vaseline | 2 | 2 |
| Squalane | 5 | 5 |
| Liquid paraffin | 10 | 10 |
| Silicone oil | 1 | 1 |
| Acylglutamic acid salt | 1 | 1 |
| Xanthane gum | 0.5 | 0.5 |
| Glycerin | 5 | 5 |
| Dipropylene glycol | 3 | 3 |
| Compound represented by formula (5) (Production Example 2) | 0.1 | — |
| Compound represented by formula (10) (Production Example 7) | — | 0.1 |
| Butylparaben | q.s. | q.s. |
| Anti-oxidant | q.s. | q.s. |
| Purified water | balance | balance |

Examples 26 and 27

Sunscreen

| Ingredients | Example 26 | Example 27 |
|---|---|---|
| Ethanol | 10 | 10 |
| Octyl methoxycinnamate | 7 | 7 |
| POE-POP-modified dimethylpolysiloxane | 2 | 2 |
| Ultrafine titanium oxide particles | 5 | 5 |
| Zinc oxide | 5 | 5 |
| Cyclic silicone | 10 | 10 |
| Diemethylpolysiloxane (6 cs) | 10 | 10 |
| Compound represented by formula (5) (Production Example 2) | 0.1 | — |
| Compound represented by formula (10) (Production Example 7) | — | 0.1 |
| Anti-oxidant | q.s. | q.s. |
| Purified water | balance | balance |

Example 28

Skin Cream

A skin cream with the following composition was prepared by a conventional method.

| Ingredients | Formulation amount (% by mass) |
|---|---|
| Beeswax | 2.0 |
| Stearic acid | 5.0 |
| Stearyl alcohol | 5.0 |
| Hydrogenated lanolin | 2.0 |
| Squalene | 20.0 |
| Sorbitan monostearate | 3.0 |
| Polyoxyethylene (20) sorbitan monostearate | 3.0 |
| Propylene glycol | 5.0 |
| Methylparaben | 0.2 |
| Compound represented by formula (17) | 0.1 |
| Purified water | Balance in the total 100 |

Example 29

Skin Cream

A skin cream with the following composition was prepared by a conventional method.

| Ingredients | Formulation amount (% by mass) |
|---|---|
| Beeswax | 2.0 |
| Stearic acid | 5.0 |
| Stearyl alcohol | 5.0 |
| Hydrogenated lanolin | 2.0 |
| Squalene | 20.0 |
| Sorbitan monostearate | 3.0 |
| Polyoxyethylene (20) sorbitan monostearate | 3.0 |
| Propylene glycol | 5.0 |
| Methylparaben | 0.2 |
| Compound represented by formula (12) (Production Example 9) | 0.5 |
| Purified water | Balance in the total 100 |

Example 30

Skin Lotion

A skin lotion with the following composition was prepared by a conventional method.

| Ingredients | Formulation amount (% by mass) |
|---|---|
| Olive oil | 10.0 |
| Isopropyl myristate | 1.0 |
| Polyoxyethylene (6) nonylphenyl ether | 0.5 |
| Propylene glycol | 1.0 |
| Glycerin | 2.0 |
| Methylparaben | 0.1 |
| Ethanol | 7.0 |
| Compound represented by formula (17) | 0.5 |
| Purified water | Balance in the total 100 |

Example 31

Bath Agent

A bathing agent with the following composition was prepared by a conventional method.

| Ingredients | Formulation amount (% by mass) |
|---|---|
| Compound represented by formula (17) | 1.0 |
| Sodium hydrogen carbonate | balance |
| Sodium carbonate | 20.0 |
| Sodium sulfate | 15.0 |
| Sodium chloride | 7.5 |
| Silicic acid anhydride | 0.5 |
| 1,3-butylene glycol | 1.0 |
| Urea | 1.0 |
| Seaweed extract | 1.0 |
| Color additive | q.s. |
| Dextrin | q.s. |
| Fragrance | q.s. |

Examples 32 to 33

Skin Cream

Skin creams with the following compositions were prepared by a conventional method.

| Ingredients | Formulation amount (% by mass) Example 32 | Formulation amount (% by mass) Example 33 |
|---|---|---|
| Compound represented by formula (17) | 0.1 | — |
| Compound represented by formula (14) (Production Example 11) | — | 0.1 |
| Stearic acid | 1 | — |
| Isostearic acid | — | 1 |
| Monostearic acid glycerin | 2 | 2 |
| Behenyl alcohol | 2 | 2 |
| Bleached beeswax | 1 | 1 |
| Cetyl myristate | 1 | 1 |
| Sorbitan sesquioleate | 1 | 1 |
| N-Stearoylphytosphingosine | 0.1 | 0.1 |
| Hydrogenated lecithin | 0.1 | 0.1 |
| Plant squalane | 5 | 5 |
| Octyldodecyl myristate | 5 | 5 |
| Phellodendron bark extract | 0.1 | 1 |
| Pyracantha fortuneana fruit extract | 0.1 | 0.3 |
| Water-soluble glycyrrhiza extract | 0.1 | 0.1 |
| 1,3-butylene glycol | 5 | 10 |
| Concentrated glycerin | 5 | 5 |
| p-Oxybenzoic acid ester | 0.2 | 0.2 |
| N-Acetylglucosamine oligomer | 0.1 | 0.1 |
| Ascorbic acid phosphate ester magnesium salt | 0.1 | 0.1 |
| Ascorbic acid phosphate ester sodium salt | 0.1 | 0.1 |
| γ-Aminobutyric acid | 0.1 | 0.1 |
| Sodium N-stearoylglutamate | 0.2 | 0.2 |
| Alkyl-modified carboxyvinyl polymer *1 | 0.05 | 0.05 |
| Nicotinic acid amide | 0.1 | 0.1 |
| Sarcosine | 0.1 | 0.1 |
| Purified water | balance | balance |

*1: PEMULEN TR-1, manufactured by B. F. Goodrich

Examples 34 and 35

Lotion

Lotions with the following compositions were prepared by a conventional method.

| Ingredients | Formulation amount (% by mass) | |
| --- | --- | --- |
| | Example 34 | Example 35 |
| Compound represented by formula (17) | 0.1 | — |
| Compound represented by formula (12) (Production Example 9) | — | 0.1 |
| Phellodendron bark extract | 0.1 | 0.3 |
| Hibiscus extract | 0.2 | 0.5 |
| Lactic acid bacteria culture medium | 0.1 | 0.1 |
| 1,3-Butylene glycol | 5 | 5 |
| Dipropylene glycol | 5 | 5 |
| Raffinose | 1 | 1 |
| Ethanol | 1 | 1 |
| Phenoxyethanol | 0.2 | 0.2 |
| Pectin | 0.05 | 0.05 |
| Xanthane gum | 0.1 | 0.1 |
| Sodium citrate | 0.05 | 0.05 |
| Equisetum arvense extract | 0.1 | 0.1 |
| Diisopropylamine dichloroacetic acid | 0.2 | 0.2 |
| γ-Amino-β-hydroxybutyric acid | 0.2 | 0.2 |
| Sodium hyaluronate | 0.001 | 0.001 |
| Dipotassium glycyrrhizate | 0.02 | 0.02 |
| Naematoloma sublateritium extract | 0.05 | 0.05 |
| Decarboxycarnosine hydrochloride | 0.05 | 0.05 |
| Fragrance | 0.02 | 0.02 |
| Purified water | balance | balance |

Examples 36 and 37

Gel

Gels with the following compositions were prepared by a conventional method.

| Ingredients | Formulation amount (% by mass) | |
| --- | --- | --- |
| | Example 36 | Example 37 |
| Compound represented by formula (13) (Production Example 10) | 0.1 | — |
| Compound represented by formula (15) (Production Example 12) | — | 0.1 |
| Decamethylcyclopentasiloxane | 10 | 10 |
| Isostearyl isostearate | 1 | — |
| Olive oil | — | 1 |
| Macadamia nut oil | 0.1 | 0.1 |
| Eucalyptus oil | 0.1 | — |
| Hexyldecanol | 1 | 0.1 |
| dl-α-tocopherol nicotinate | — | 0.1 |
| Polyoxyethylene (60) hydrogenated castor oil | 2 | 2 |
| Spherical silicone powder *2 | 1 | 1 |
| Phellodendron bark extract | 0.1 | 1 |
| Water-soluble chlorophyll | 0.02 | 0.02 |
| Salvia extract | — | 0.3 |
| 1,3-Butylene glycol | 5 | 10 |
| Sorbitol liquid | 3 | 3 |
| Polyethylene glycol 4000 | 1 | 1 |
| Carboxyvinyl polymer | 0.2 | 0.2 |
| Sugar ceramide *3 | 0.1 | 0.1 |
| p-Oxybenzoic acid ester | 0.2 | 0.2 |
| Mevalonolactone | 0.5 | 0.5 |
| Edetic acid salt | 0.02 | 0.02 |
| Potassium hydroxide | 0.05 | 0.05 |
| Purified water | balance | balance |

*2: Tospearl, manufactured by GE Toshiba Silicone Co., Ltd.
*3: Bioceramide, manufactured by Kibun Food Chemical Co., Ltd.

Examples 38 and 39

Lipophilic Cream

Lipophilic creams with the following compositions were prepared by a conventional method.

| Ingredients | Formulation amount (% by mass) | |
| --- | --- | --- |
| | Example 38 | Example 39 |
| Compound represented by formula (17) | 0.1 | — |
| Compound represented by formula (15) (Production Example 12) | — | 0.1 |
| Co-modified silicone *4 | 2 | 2 |
| Polyeoxethylene-modified silicone dispersion *5 | — | 2 |
| Squalane | 2 | 2 |
| Decamethylcyclopentasiloxane | 15 | 20 |
| Methylpolysiloxane | 5 | 2 |
| Cholesteryl branched long chain fatty acid ester *6 | 1 | 1 |
| Silicone elastomer dispersion *7 | 5 | 2 |
| Phellodendron bark extract | 1 | 1 |
| Glycyrrhiza extract | 0.1 | 0.1 |
| Water-soluble chlorophyll | 0.02 | 0.02 |
| Sodium chloride | 1 | 1 |
| Dipropylene glycol | 5 | 5 |
| Concentrated glycerin | 5 | 5 |
| Raffinose | 1 | 1 |
| p-Oxybenzoic acid ester | 0.3 | 0.3 |
| N-Methyl-L-serine | 0.5 | 0.5 |
| Purified water | balance | balance |

*4: ABIL EM90, manufactured by Goldschmidt A.G.
*5: Silicone BY 22-008, manufactured by Dow Corning Toray Silicone
*6: YOFCO CLE-NH, manufactured by Nippon Fine Chemical Co., Ltd.
*7: Trefil, manufactured by Dow Corning Toray Silicone Co., Ltd.

Examples 40 and 41

Sunscreen

Sunscreens with the following compositions were prepared by a conventional method.

| Ingredients | Formulation amount (% by mass) | |
| --- | --- | --- |
| | Example 40 | Example 41 |
| Compound represented by formula (17) | 0.1 | — |
| Compound represented by formula (14) (Production Example 11) | — | 0.1 |
| Dioctyl ether | 10 | 10 |
| Co-modified silicone *4 | 2 | 2 |
| Glyceryl tri-2-ethylhexanoate | 5 | 5 |
| Hydrogenated oil | 0.1 | 0.1 |

-continued

| Ingredients | Formulation amount (% by mass) | |
|---|---|---|
| | Example 40 | Example 41 |
| Methylphenylpolysiloxane | 3 | 3 |
| Phytosteryl macadamia nut fatty acid | 1 | 1 |
| 2-Ethylhexyl p-methoxycinnamate | — | 7 |
| Titanium oxide | 5 | 5 |
| Zinc oxide | 5 | 5 |
| Phellodendron bark extract | 1 | 1 |
| Magnesium chloride | 1 | 1 |
| 1,3-Butylene glycol | 5 | 5 |
| Phenoxyethanol | 0.3 | 0.3 |
| Hibiscus extract | 1 | 1 |
| Aloe extract | 0.1 | 0.1 |
| Yeast extract *8 | 1 | 1 |
| Purified water | balance | balance |

*4: ABIL EM90, manufactured by Goldschmidt A.G.
*8: Dismutin, manufactured by PentaFarm Ltd.

Example 42

Face Lotion

| Ingredients | Formulation amount (% by mass) |
|---|---|
| Ethanol | 10 |
| Polyoxyethylene (60) hydrogenated castor oil | 1 |
| Glycerin | 3 |
| 1,3-Butylene glycol | 2 |
| Dipropylene glycol | 3 |
| Polyethylene glycol 1500 | 1 |
| Phosphoric acid salt | q.s. |
| Edetic acid salt | q.s. |
| Methylparaben | q.s. |
| Compound represented by formula (15) (Production Example 12) | 0.1 |
| Anti-oxidant | q.s. |
| Purified water | balance |

Examples 43 and 44

Emulsion

| Ingredients | Formulation amount (% by mass) | |
|---|---|---|
| | Example 43 | Example 44 |
| Stearic acid | 1 | 1 |
| Stearic acid glycerin ester | 2 | 2 |
| Cetanol | 1 | 1 |
| Cholesterol | 0.5 | 0.5 |
| Vaseline | 2 | 2 |
| Squalane | 5 | 5 |
| Liquid paraffin | 5 | 5 |
| Silicone oil | 1 | 1 |
| Acylglutamic acid salt | 1 | 1 |
| Xanthane gum | 0.5 | 0.5 |
| Glycerin | 2 | 2 |
| Dipropylene glycol | 3 | 3 |
| Compound represented by formula (17) | 0.1 | — |
| Compound represented by formula (15) (Production Example 12) | — | 0.1 |
| Butylparaben | q.s. | q.s. |

-continued

| Ingredients | Formulation amount (% by mass) | |
|---|---|---|
| | Example 43 | Example 44 |
| Anti-oxidant | q.s. | q.s. |
| Purified water | balance | balance |

Examples 45 and 46 (Cream)

| Ingredients | Formulation amount (% by mass) | |
|---|---|---|
| | Example 45 | Example 46 |
| Stearic acid | 2 | 2 |
| Stearic acid glycerin ester | 2 | 2 |
| Cetanol | 3 | 3 |
| Cholesterol | 0.5 | 0.5 |
| Vaseline | 2 | 2 |
| Squalane | 5 | 5 |
| Liquid paraffin | 10 | 10 |
| Silicone oil | 1 | 1 |
| Acylglutamic acid salt | 1 | 1 |
| Xanthane gum | 0.5 | 0.5 |
| Glycerin | 5 | 5 |
| Dipropylene glycol | 3 | 3 |
| Compound represented by formula (13) (Production Example 10) | 0.1 | — |
| Compound represented by formula (15) (Production Example 12) | — | 0.1 |
| Butylparaben | q.s. | q.s. |
| Anti-oxidant | q.s. | q.s |
| Purified water | balance | balance |

Examples 47 and 48

Sunscreen

| Ingredients | Formulation amount (% by mass) | |
|---|---|---|
| | Example 47 | Example 48 |
| Ethanol | 10 | 10 |
| Octyl methoxycinnamate | 7 | 7 |
| POE-POP-modified dimethylpolysiloxane | 2 | 2 |
| Ultrafine titanium oxide particles | 5 | 5 |
| Zinc oxide | 5 | 5 |
| Cyclic silicone | 10 | 10 |
| Diemethylpolysiloxane (6cs) | 10 | 10 |
| Compound represented by formula (13) (Production Example 10) | 0.1 | — |
| Compound represented by formula (15) (Production Example 12) | — | 0.1 |
| Anti-oxidant | q.s. | q.s. |
| Purified water | balance | balance |

INDUSTRIAL APPLICABILITY

As described above, it is made clear that the invention can provide an epidermal hyaluronic acid production-promoting agent which can be simply and easily synthesized. The invention makes it possible to prevent the skin from aging (to retain vital, elastic, and moist skin).

The invention claimed is:

1. A skin external preparation comprising an N-acetylglucosamine derivative of formula (3):

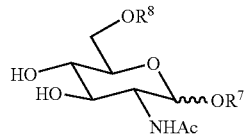

formula (3)

wherein $R^7$ is an alkyl group having 2 to 18 carbon atoms; $R^8$ is an acyl group having 2 to 18 carbon atoms; and the steric structure at position 1 may be α or β.

2. The skin external preparation of claim 1, wherein the N-acetylglucosamine derivative of the formula (3) is an N-acetylglucosamine derivative of formula (6):

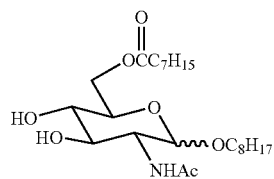

formula (6)

wherein the steric structure at position 1 may be α or β.

* * * * *